US012208217B1

United States Patent
Aslam

(10) Patent No.: US 12,208,217 B1
(45) Date of Patent: Jan. 28, 2025

(54) DEEP LEARNING ENABLED HAPTIC HOLOGRAPHIC ENVIRONMENT

(71) Applicant: United Arab Emirates University, Al Ain (AE)

(72) Inventor: Zulfiqar Aslam, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 18/645,735

(22) Filed: Apr. 25, 2024

(51) Int. Cl.
| | |
|---|---|
| *A61M 21/02* | (2006.01) |
| *A61H 23/02* | (2006.01) |
| *A61M 21/00* | (2006.01) |
| *G06F 3/01* | (2006.01) |
| *G06N 20/00* | (2019.01) |
| *G06T 19/00* | (2011.01) |

(52) U.S. Cl.
CPC ......... *A61M 21/02* (2013.01); *A61H 23/0245* (2013.01); *G06F 3/012* (2013.01); *G06F 3/016* (2013.01); *G06N 20/00* (2019.01); *G06T 19/00* (2013.01); *A61M 2021/0022* (2013.01); *A61M 2205/3303* (2013.01); *A61M 2205/80* (2013.01); *A61M 2230/63* (2013.01)

(58) Field of Classification Search
CPC .......... A61M 21/02; A61M 2021/0022; A61M 2205/3303; A61M 2205/80; A61M 2230/63; A61H 23/0245; G06F 3/012; G06F 3/016; G06N 20/00; G06T 19/00
See application file for complete search history.

(56) References Cited

U.S. PATENT DOCUMENTS

| | | | | |
|---|---|---|---|---|
| 11,048,329 | B1 * | 6/2021 | Lee | ......................... G06F 3/011 |
| 2022/0373795 | A1 * | 11/2022 | Latapie | ................. H04L 65/403 |

* cited by examiner

*Primary Examiner* — Carrie R Dorna
*Assistant Examiner* — Joshua Daryl D Lannu
(74) *Attorney, Agent, or Firm* — MH2 Technology Law Group, LLP

(57) ABSTRACT

A haptic holographic environment. The haptic holographic environment includes a holographic projector; a plurality of piezoelectric transducers; a plurality of sensors for sensing a user's movement and biometric data; a processor; and a deep learning module comprising a deep learning model. The deep learning model is pre-trained with input data associated with an individual, such that the processor can control the holographic projector to project a hologram of the individual. The plurality of piezoelectric transducers emits ultrasound waves to emulate physical sensation for the user when interacting with the hologram. The processor is configured to receive the user's movement and biometric data and adjust the hologram in response to the user's movement and biometric data such that the user's biometric data moves towards a target value. A method of controlling the output of a hologram projection is also provided.

19 Claims, 2 Drawing Sheets

DEEP LEARNING ENABLED HAPTIC HOLOGRAPHIC ENVIRONMENT

FIELD

The present disclosure relates to haptic holographic environments. More specifically, but not exclusively, the present disclosure relates to deep learning enabled haptic holographic environments.

BACKGROUND

Background description includes information that will be useful in understanding the present invention. It is not an admission that any of the information provided herein is prior art or relevant to the presently claimed invention, or that any publication specifically or implicitly referenced is prior art.

Stress, anxiety and depression are common and natural to the grieving process. After the loss of a loved one, emotional distancing from a family member or a close friend due to a disagreement is common. Adults as well as children may experience a complicated grief or anxiety disorder. Grieving people find themselves panicking or worrying excessively about what or whom else they could lose in the future, leading to various mental disorders.

One of the disorders that may occur after the loss of a loved one is depressive disorder (depression). The causes of depression include complex interactions between social, psychological and biological factors.

According to the World Health Organization (WHO), an estimated 3.8% of the global population experiences depression, including 5% of adults (4% among men and 6% among women), and 5.7% of adults older than 60 years. Approximately 280 million people in the world have depression. Depression is about 50% more common among women than among men. Due to the COVID-19 pandemic, global prevalence of anxiety and depression has increased by a large 25%, according to the World Health Organization (WHO).

Another disorder that may occur after the loss of a loved one is anxiety disorder. Anxiety disorder is a feeling of fear, dread, and uneasiness, causing restlessness, sweating and a rapid heartbeat.

According to the American Psychiatric Organization, nearly 30% of adults at some point in their lives will be affected with the various forms of anxiety, such as generalized anxiety disorder, panic disorder, specific phobias, social anxiety disorder, separation anxiety disorder, and selective mutism (inability to speak).

Additionally, the bereaved may experience stress, which is a feeling of emotional or physical tension. Stress may manifest as emotional distancing from a family member or a close friend. These are life's most stressful events and can cause a major emotional crisis. Grief reactions lead to complex and psychological symptoms. The person who experiences a loss may have a range of feelings, including shock, numbness, sadness, denial, anger, guilt, helplessness, depression and anxiety.

Currently, there are a number of traditional psychiatric therapies available to assist a person experiencing loss. However, there is scope for improvement in both measurement of the progress of the user, and in the creation of positive outcomes for the user.

Therefore, the present disclosure seeks to provide a method utilizing 3D virtual holographic projections that responds to users who experience intense grief symptoms.

SUMMARY

According to a first aspect of the present disclosure, there is provided a haptic holographic environment. The haptic holographic environment comprises a holographic projector; a plurality of piezoelectric transducers; a plurality of sensors for sensing a user's movement and biometric data; a processor; and a deep learning module comprising a deep learning model. The deep learning model is pre-trained with input data associated with an individual, such that the processor can control the holographic projector to project a hologram of the individual. The plurality of piezoelectric transducers emits ultrasound waves to emulate physical sensation for the user when interacting with the hologram. The processor is configured to receive the user's movement and biometric data and adjust the hologram in response to the user's movement and biometric data such that the user's biometric data moves towards a target value.

Advantageously, the system does not require the user to wear a holographic projection device such as a virtual reality headset, which is cumbersome and reduces the level of immersion for the user. Additionally, the system does not require the user to wear apparatus to provide physical feedback to the user, as the piezoelectric transducers are able to mimic the sensation of touch for the user without requiring the user to wear any apparatus.

The deep learning model may be updated to account for deviation between the user's biometric data and the target value.

The projected hologram of the individual may be configured through the deep learning model to emulate characteristics of the individual. The characteristics of the individual may comprise movement and speech.

The input data associated with an individual may comprise media comprising one or more of video, audio, and/or images.

The speech characteristic of the individual may comprise one or more of communication styles, accents, languages, and/or dialects.

The biometric data may comprise one or more of heart activity, skin activity, brain activity, and/or temperature.

The target value may be predetermined. The target value may be predetermined by a medical professional.

The plurality of sensors may comprise motion sensors.

The processor may be configured to control the hologram in response to the user's movement data, such that the hologram is adjusted to respond to the user's movement while emulating the characteristics of the individual.

The input data associated with an individual may be historical data.

According to a second aspect of the present disclosure, there is provided a method of controlling the output of a hologram projection. The method comprises the steps of: training a deep learning model with input data associated with an individual; projecting, using a holographic projector and as a function of the deep learning model, a hologram of the individual; emulating physical sensation for the user when interacting with the hologram by using piezoelectric transducers to emit ultrasound waves; receiving, using a plurality of sensors, a user's movement and biometric data; and adjusting the hologram in response to the user's movement and biometric data such that the user's biometric data moves towards a target value.

The hologram may emulate characteristics of the individual.

The characteristics of the individual may comprise movement and speech.

The adjusting may comprise controlling the hologram in response to the user's movement data, such that the hologram is adjusted to respond to the user's movement while emulating the characteristics of the individual.

The user's movement data may comprise facial expressions.

The characteristics of the individual may comprise smell.

The method may comprise a step of dispersing a fragrance to emulate the smell of the individual.

BRIEF DESCRIPTION OF THE DRAWINGS

The manner in which the above-recited features of the present invention is understood in detail, a more particular description of the invention, briefly summarized above, may be had by reference to embodiments, some of which are illustrated in the appended drawings. It is to be noted, however, that the appended drawings illustrate only typical embodiments of the present disclosure and are therefore not to be considered limiting of its scope, for the present disclosure may admit to other equally effective embodiments.

The foregoing and other objects, features and advantages of the present invention, as well as the invention itself, will be more fully understood from the following description of preferred embodiments, when read together with the accompanying drawings.

DETAILED DESCRIPTION

The present disclosure relates to the field of haptic holographic environments, and more particularly to deep learning enabled haptic holographic environments.

Figure 1:
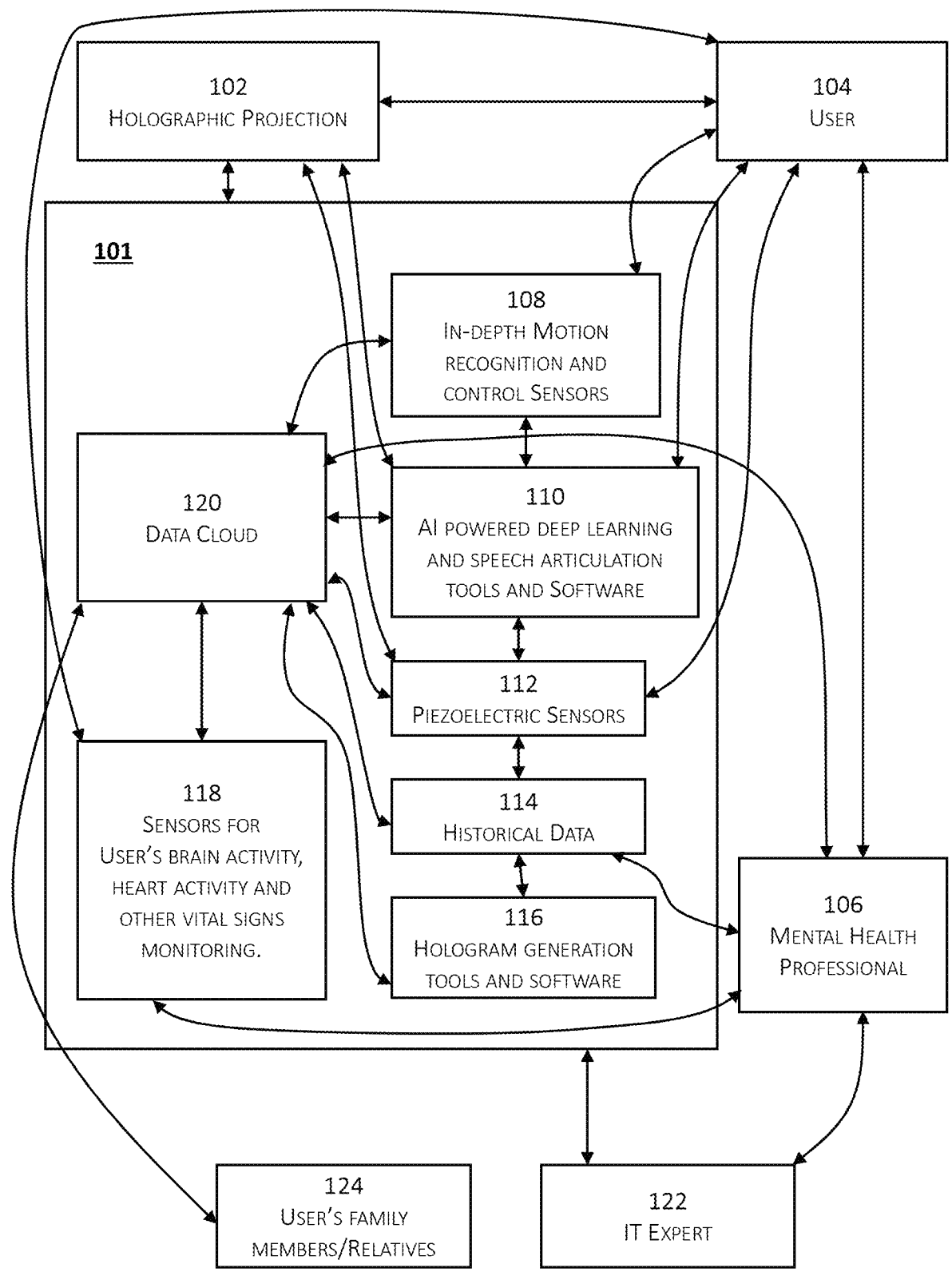
FIG. 1 shows a schematic model for the holographic system.
Figure 2:
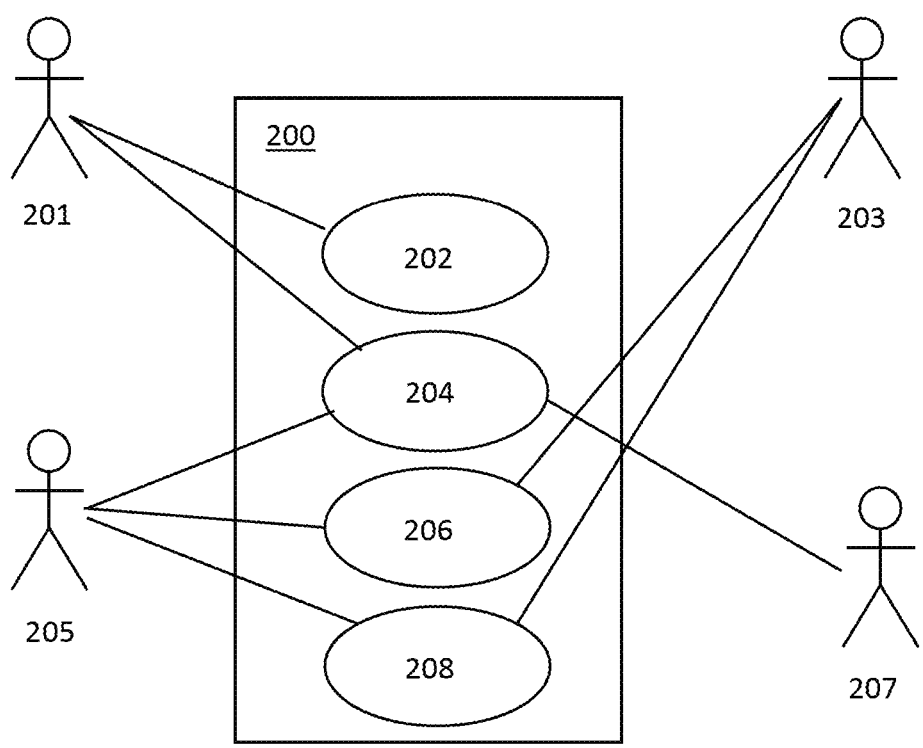
FIG. 2 shows a diagram outlining the interactions between users of the holographic system.

The principles of the present invention and their advantages are best understood by referring to FIG. 1 to FIG. 2. In the following detailed description of illustrative or exemplary embodiments of the disclosure, specific embodiments in which the disclosure may be practiced are described in sufficient detail to enable those skilled in the art to practice the disclosed embodiments. The following detailed description is, therefore, not to be taken in a limiting sense, and the scope of the present disclosure is defined by the appended claims and equivalents thereof. References within the specification to "one embodiment," "an embodiment," "embodiments," or "one or more embodiments" are intended to indicate that a particular feature, structure, or characteristic described in connection with the embodiment is included in at least one embodiment of the present disclosure.

FIG. 1 shows a schematic model for the holographic system.

The holographic system comprises the system 101, the holographic projection 102, the user, 104, the mental health professional, 106, an IT expert, 122, and parties related to the user 124. The interaction of these various entities are shown in FIG. 1.

The system 101 includes a data cloud 120. The data cloud 120 receives and stores data from a plurality of data sources, such as motion recognition and control sensors 108, piezoelectric sensors 112, historical data 114, and biometric sensors 118.

The motion recognition and control sensors 108 are, in embodiments, ultra leap 3Di in-depth motion sensors. This technology enables the user to provide movement inputs in the form of natural signs/movements of the user's body parts such as hands, facial expressions and communication language. In embodiments, the user is able to provide inputs in the form of natural sign language.

The piezoelectric sensors 112 include piezoelectric transducers. The transducers produce ultrasonic waves that can be detected as touch by the user. A processor of the system 101 is able to control the outputs of the piezoelectric transducers such that the user experiences touch sensations when interacting with the holographic projection 102, which adds to the immersion of the user in the system, improving outcomes.

Historical data 114 is in the form of various media such as audio, video, and images, for example. The AI-powered deep learning model 110 takes the historical data, which may be associated with an individual that has passed away, for example, and builds a model based on that data 114. The processor is then able to use the model that has been built by the deep learning software 110 and generate a representative hologram 102 of the individual that has passed.

Since the model 110 is trained on historical data 114, the holographic projection 102 is able to mimic characteristics of the individual such as speech, accent, language, mannerisms, facial expressions, manner of speech, and movement.

The hologram generation tools and software 116 enable the generation of the holograms based on the AI-powered model.

The biometric sensors 118 detect various biometric signals such as brain activity, heart activity, skin activity, body temperature, and other vital signs. These biometric signals are measured against predetermined values. These predetermined values are target values.

The system measures the biometric signals of the user and compares them to the target values. The system then adjusts parameters of the hologram such that the biometric signal data approaches the target values. For example, if the objective is to reduce stress, the hologram may be adjusted to be more calming and reassuring to the user, to reduce stress.

The deep learning software 110 is able to learn how different adjustments to the hologram affect the biometric signals of the user, such that future adjustments can be made to the hologram more accurately to achieve the desired outcome depending on the specific user 104.

Family members of the user 124 also provide data into the data cloud.

An IT expert 122 interacts with the system 101 to ensure that the system is functioning as intended. A mental health professional 106 manages the input of historical data 114, liaises with the user 104, and monitors the biometric data being received by the sensors 118. The mental health professional may also set the target values for the biometric data to measure the success of the outcomes.

Symptoms of loss such as stress, anxiety and depression are measured during the interaction of the user with the holographic avatar of the deceased ones in front of the user in the air, communicating and performing as programed by the technology experts based on the historical data of the loved ones in the form of images, videos, voice, signature moves, dialect and languages.

Furthermore, the environment also is integrated with devices to disperse artificial fragrance, spray of perfume and scent of the avatar/impersonated character simultaneously as programmed.

Moreover, artificial touch sensation (such as touching the hand or even hugging a hologram in the mid-air with a feeling of warmth) is applied using piezoelectric transducers (producing ultrasound waves for sensations i.e., vibration, touch and force).

No wearable is required by the user as all the signals are taken as an input by an ultra-leap 3D in-depth motion sensor in front of the user and are translated and processed through AI based algorithms written in Leap.js or Node.js programming modules referred to as Neuro-Linguistic Programming (NLP).

Embodiments of the present disclosure provide a real-time, immersive, holographic environment for the user, where the hologram reacts and responds in real-time to actions/sounds/speech of the user, based on AI-powered deep learning software that has been trained on historic data based on an individual to be emulated by the hologram.

FIG. 2 shows a diagram outlining the interactions between users of the holographic system.

The haptic-holographic applied system 200 comprises four main pillars. The pillars include control and maintenance 202, historical data 204, the hologram 206, and emotional activities 208.

For the maintenance of accuracy, precision, and ethics, different users are only able to interact with necessary pillars of the system (rather than all of them at once, for example).

The IT expert 201 only interacts with the control and maintenance 202, and the historical data 204.

The user 203 interacts with the hologram 206 and emotional activities 208.

The mental health expert 204 interacts with the historical data 204, the hologram 206, and the emotional activities 208.

The relatives of the user 207 only interact with the historical data.

It will be apparent that this interaction of various actors in the system is consistent with the schematic of FIG. 1.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents. The disclosures and the description herein are intended to be illustrative and are not in any sense limiting the present disclosure, defined in scope by the following claims.

Many changes, modifications, variations and other uses and applications of the present disclosure will become apparent to those skilled in the art after considering this specification and the accompanying drawings, which disclose the preferred embodiments thereof. All such changes, modifications, variations and other uses and applications, which do not depart from the spirit and scope of the present disclosure, are deemed to be covered by the invention, which is to be limited only by the claims which follow.

The invention claimed is:

1. A system to create a haptic holographic environment, the system comprising:
    a holographic projector;
    a plurality of piezoelectric transducers;
    a plurality of sensors for sensing a user's movement and biometric data;
    a processor; and
    a deep learning module comprising a deep learning model;
    wherein the deep learning model is pre-trained with input data associated with an individual, such that the processor can control the holographic projector to project a hologram of the individual;
    wherein the plurality of piezoelectric transducers emits ultrasound waves to emulate physical sensation for the user when interacting with the hologram, and
    wherein the processor is configured to receive the user's movement and biometric data and adjust the hologram in response to the user's movement and biometric data such that the user's biometric data moves towards a target value.

2. The system as claimed in claim 1, wherein the deep learning model is updated to account for deviation between the user's biometric data and the target value.

3. The system as claimed in claim 1, wherein the projected hologram of the individual is configured through the deep learning model to emulate characteristics of the individual.

4. The system as claimed in claim 3, wherein the characteristics of the individual comprise movement and speech.

5. The system as claimed in claim 4, wherein the speech characteristic of the individual comprises one or more of communication styles, accents, languages, and/or dialects.

6. The system as claimed in claim 4, wherein the processor is configured to control the hologram in response to the user's movement data, such that the hologram is adjusted to respond to the user's movement while emulating the characteristics of the individual.

7. The system as claimed in claim 1, wherein the input data associated with the individual comprises media comprising one or more of video, audio, and/or images.

8. The system as claimed in claim 1, wherein the biometric data comprises one or more of heart activity, skin activity, brain activity, and/or temperature.

9. The system as claimed in claim 1, wherein the target value is predetermined.

10. The system as claimed in claim 9, wherein the target value is predetermined by a medical professional.

11. The system as claimed in claim 1, wherein the plurality of sensors comprises motion sensors.

12. The system as claimed in claim 1, wherein the input data associated with the individual is historical data.

13. A method of controlling output of a hologram projection, the method comprising the steps of:
    training a deep learning model with input data associated with an individual;
    projecting, using a holographic projector and as a function of the deep learning model, a hologram of the individual;
    emulating physical sensation for a user when interacting with the hologram by using piezoelectric transducers to emit ultrasound waves;
    receiving, using a plurality of sensors, the user's movement and biometric data; and
    adjusting the hologram in response to the user's movement and biometric data such that the user's biometric data moves towards a target value.

14. The method as claimed in claim 13, wherein the hologram emulates characteristics of the individual.

15. The method as claimed in claim 14, wherein the characteristics of the individual comprise movement and speech.

16. The method as claimed in claim 15, wherein the adjusting comprises controlling the hologram in response to the user's movement data, such that the hologram is adjusted to respond to the user's movement while emulating the characteristics of the individual.

17. The method as claimed in claim 16, wherein the user's movement data comprises facial expressions.

18. The method as claimed in claim 15, wherein the characteristics of the individual comprise smell.

19. The method as claimed in claim 18, wherein the method comprises a step of dispersing a fragrance to emulate the smell of the individual.

* * * * *